United States Patent [19]

Hök et al.

[11] Patent Number: 4,459,841
[45] Date of Patent: Jul. 17, 1984

[54] MINIATURE PRESSURE TRANSDUCER

[75] Inventors: Bertil Hök, Västeras; Olof Ekström, Brottby, both of Sweden

[73] Assignee: Siemens Aktiengesellschaft, Berlin & Munich, Fed. Rep. of Germany

[21] Appl. No.: 389,377

[22] Filed: Jun. 17, 1982

[30] Foreign Application Priority Data

Jul. 31, 1981 [DE] Fed. Rep. of Germany ....... 3130367

[51] Int. Cl.³ .......................... G01L 9/02; G01L 27/02
[52] U.S. Cl. ........................................ 73/4 R; 73/753; 128/673
[58] Field of Search ........................ 73/753, 756, 4 R; 128/672, 673, 674, 675, 748

[56] References Cited

U.S. PATENT DOCUMENTS

| 4,261,208 | 4/1981 | Hök et al. | 73/753 |
| 4,297,890 | 11/1981 | Hök | 73/753 |
| 4,384,470 | 5/1983 | Fiore | 73/4 R |
| 4,413,528 | 11/1983 | Hök et al. | 73/753 |

Primary Examiner—Gerald Goldberg
Assistant Examiner—John E. Chapman, Jr.
Attorney, Agent, or Firm—Hill, Van Santen, Steadman & Simpson

[57] ABSTRACT

In an exemplary embodiment, a measuring cell is disposed in an outer tube. A chamber in the outer tube adjacent the measuring cell can be directly connected via an opening to the liquid in a liquid vessel whose pressure is to be measured. In order to also be able to calibrate the pressure transducer at any time in the liquid vessel, an elastic container is inventively disposed in the chamber, the container being connected to a connecting line likewise lying in the outer tube for the purpose of filling and emptying. In its filled state, the container closes the opening of the chamber without interrupting the connection between a fluid line used for calibration and the measuring cell.

2 Claims, 2 Drawing Figures

MINIATURE PRESSURE TRANSDUCER

BACKGROUND OF THE INVENTION

The invention relates to a miniature pressure transducer for generating an electrical signal which corresponds to a liquid pressure to be measured in a liquid vessel, comprising a measuring cell disposed in an outer tube, said measuring cell exhibiting means for generating an electrical magnitude corresponding to the pressure to be measured, as well as comprising a fluid line for the passage of liquid to a chamber which is formed, on the one hand, by the mouth of the fluid line and/or by the measuring cell and, on the other hand, by the inside wall of the outer tube and which can be directly connected to the liquid in the liquid vessel via an opening.

A miniature pressure transducer of this type is known from the U.S. Pat. Nos. 4,261,208 and 4,297,890, the disclosures of these patents being incorporated herein by reference. This pressure transducer, which is provided for physiological pressure measurements, exhibits in the case of U.S. Pat. No. 4,261,208, and endface tube opening which lies frontally opposite the opening of the measuring cell. Before the pressure transducer is introduced into a liquid vessel, it must first be filled with liquid and then be calibrated. A possible disadvantage in calibrating at this point in time is that the output signal of the pressure transducer can change before it is situated at the location to be measured in the liquid vessel. This said disadvantage of the pressure transducer can be partially avoided in that it is periodically removed from the vessel and is re-calibrated. This, however, is involved and is inconvenient for a patient.

SUMMARY OF THE INVENTION

The object of the invention is to create a pressure transducer of the type initially cited in which calibration can be undertaken at any time directly in the liquid vessel.

This object is inventively achieved in that an expansible container with at least partially elastic walls is disposed in the chamber, said container being connected to a connecting line for filling and emptying which likewise lies in the outer tube; and in that the container, in its filled state, closes the opening of the chamber without interrupting the connection between the fluid line and the measuring cell. As a result of the container serving as a valve, the pressure transducer can now be directly calibrated in the liquid vessel.

In the following, the invention is described in greater detail on the basis of an exemplary embodiment shown on the accompanying drawing sheet; and other objects, features and advantages will be apparent from this detailed disclosure and from the appended claims.

DETAILED DESCRIPTION

Figure 1:
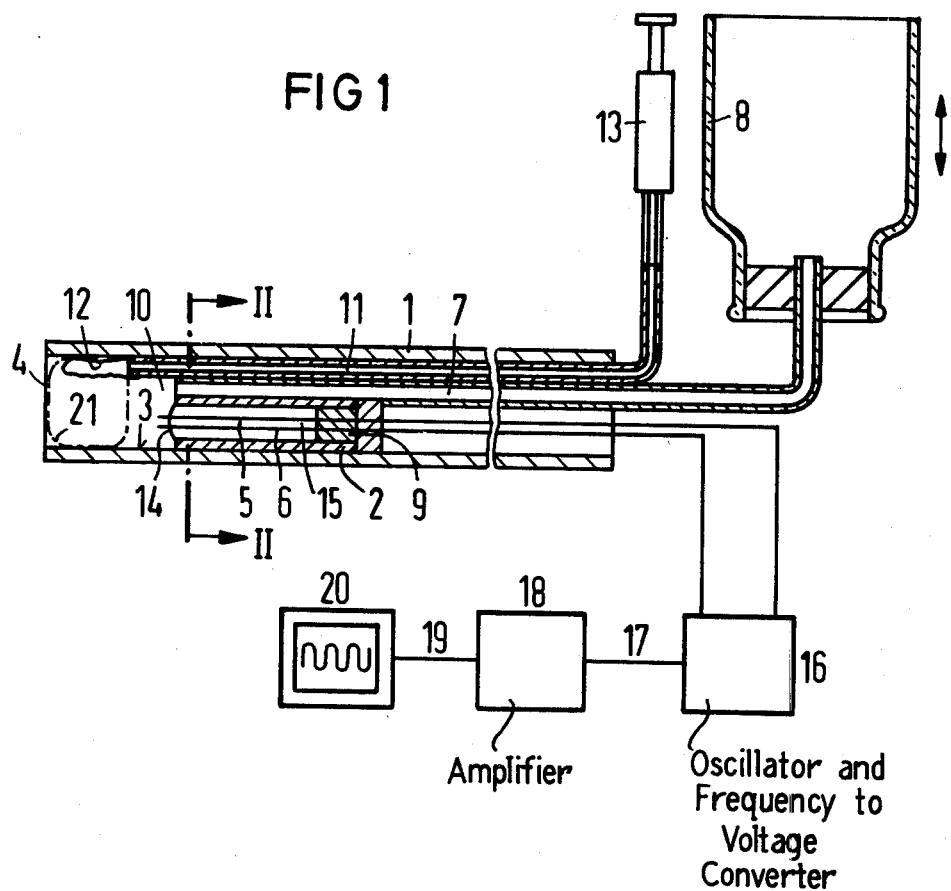
FIG. 1 shows a longitudinal section through an inventive pressure transducer.

FIG. 1 shows that the miniature pressure transducer exhibits an outer tube 1 as well as an inner tube 2 which forms the measuring cell and is surrounded by the outer tube. The measuring cell 2 is disposed in the outer tube 1 and is secured to its inside wall 3. The measuring cell 2 is closed at its end 9 facing away from the measuring end and facing away from the end face 4 of the pressure transducer. Moreover, the measuring cell 2 terminates at a distance from the end face 4 of the outer tube 1. Two electrodes 5 and 6 of platinum are disposed in the measuring cell 2 and extend in the longitudinal direction of the tube at a distance from each other, the electrodes projecting from the open end of the measuring cell 2 and being connected to a circuit arrangement to be described later for measuring the resistance between them. A fluid line 7 to which a liquid container 8 with a salt solution is connected, leads into the outer tube 1. The orifice of the fluid line 7 and of the measuring cell 2 on the one hand and the inside wall 3 of the outer tube 1 and the end face 4 of the pressure transducer on the other hand form a chamber 10. A further connecting line 11 extends into the outer tube 1, its one end adjacent the chamber 10 being provided with an expansible container 12 with at least partially elastic walls. For the purpose of filling and emptying the container serving as an inflatable balloon, an inflation or expansion control means, for example, an injection syringe 13, is provided, being connected to the free end of the connecting line 11. In the filled state of the balloon 12, the end-face opening of the chamber 10 is closed without interrupting the connection between the fluid line 7 and the measuring cell 2.

When a measurement of blood pressure is to be undertaken, the pressure transducer must be filled with salt solution before it is introduced to the measuring location, for example, into a blood vessel. To that end, salt solution flows from the liquid container 8 via the fluid line 7 into the chamber 10 and expresses the air existing in the pressure transducer into the atmosphere via the opening of the end face 4. Because of the small dimensions of the pressure transducer, the salt solution, depending on the pressure of the liquid container, flows into the chamber and fills it. As a result of the design and position of the measuring cell 2, the air situated therein is not removed. A meniscus 14 is formed in the area of the free end of the measuring cell.

The pressure transducer is now introduced into a blood vessel of a patient for a blood pressure measurement, whereby the gas volume 15 enclosed in the measuring cell 2 changes. The respective gas volume corresponds to the pressure of the salt solution and, thus, to the pressure to be measured and, as described in U.S. Pat. Nos. 4,261,208 and 4,297,890, is converted into an electrical signal in an oscillator and frequency to voltage converter device 16. The device 16 is in turn connected over the connection 17 to an amplifier 18 for amplifying the signals from the device 16. The amplifier 18 is in turn connected over the connection 19 to the recording device 20 for recording the test results.

The pressure transducer can now be directly calibrated in the blood vessel before and/or between the measurements. This ensues in that, by means of the injection syringe 13, air is introduced over the connecting line 11 into the balloon 12 until said balloon closes the opening at the end face 4 of the pressure transducer, as shown by the dot-dash line 21. Without influence of the ambient pressure in the vessel, a known salt solution pressure existing in the liquid container 8 can be supplied to the meniscus 14 of the measuring cell 2, whereby calibration ensues. After calibration, the balloon 12 is emptied in that the air is suctioned out of the balloon 12 by means of the injection syringe. A blood pressure test can subsequently ensue.

In the manner described above, the pressure transducer can be calibrated at any time, given measurement in a blood vessel, without having to be removed from said blood vessel.

Figure 2:
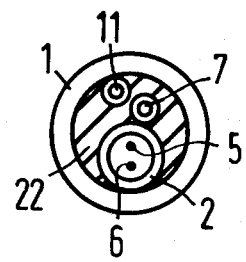
FIG. 2 is a cross-sectional view through the pressure transducer according to FIG. 1 taken along the line II—II.

It is shown in FIG. 2 that the measuring cell 2 and the lines 7 and 11 are embedded in silicon rubber 22 up to the region of chamber 10.

It will be apparent that many modifications and variations may be made without departing from the scope of the teachings and concepts of the present invention.

We claim as our invention:

1. A miniature pressure transducer for generating an electrical signal which corresponds to a liquid pressure to be measured in a liquid vessel, comprising an outer tube, a measuring cell disposed in the outer tube, said measuring cell having means for generating an electrical magnitude corresponding to the pressure to be measured, said outer tube having a chamber in fluid communication with the measuring cell, and a fluid line for the passage of liquid to the chamber, and means for connecting said chamber directly to the liquid in the liquid vessel comprising an opening in the outer tube, characterized in that an expansible container is disposed in the chamber, said container having a connecting line lying in the outer tube and connecting with the interior of said container, and expansion control means for coupling with said connecting line remote from said container for the purpose of filling and emptying said container; and in that said container in a filled condition of the container being expanded to close the opening of the outer tube and thereby to shut off fluid communication between the liquid in the chamber and the liquid in the liquid vessel without interrupting fluid communication between the fluid line and the measuring cell whereby the transducer can be calibrated by means of a predetermined liquid pressure supplied to said chamber via said fluid line.

2. A miniature pressure transducer according to claim 1, characterized in that an inflatable balloon serves as the container, a free end of the connecting line being connectible to said expansion control means.

* * * * *